United States Patent
Lemay et al.

Patent Number: 5,374,260
Date of Patent: Dec. 20, 1994

[54] UNITIZED SANITARY NAPKIN

[75] Inventors: Martin Lemay, Montreal; Christiane Lariviere, Lavaltrie; Daniel Comeau, Lachenaie; Yvon Levesque, Montreal, all of Canada

[73] Assignee: Johnson & Johnson Inc., Canada

[21] Appl. No.: 169,951

[22] Filed: Dec. 20, 1993

Related U.S. Application Data

[63] Continuation of Ser. No. 808,130, Dec. 13, 1991, abandoned, which is a continuation-in-part of Ser. No. 601,491, Oct. 22, 1990, abandoned, which is a continuation of Ser. No. 389,710, Aug. 4, 1989, abandoned.

[51] Int. Cl.⁵ .................. A61F 13/15; A61F 13/20
[52] U.S. Cl. .................. 604/378; 604/358; 604/367; 604/371; 604/379; 604/380; 604/385.1
[58] Field of Search ............ 604/358, 366, 367, 370, 604/371, 378, 379, 380, 385.1

[56] References Cited

U.S. PATENT DOCUMENTS

| | | | |
|---|---|---|---|
| 2,788,003 | 4/1957 | Morin | 128/284 |
| 3,768,480 | 10/1973 | Mesek et al. | 604/365 |
| 4,102,340 | 7/1978 | Mesek et al. | 128/287 |
| 4,170,515 | 10/1979 | Lalancette et al. | 162/92 |
| 4,186,165 | 1/1980 | Aberson et al. | 264/112 |
| 4,196,245 | 4/1980 | Kitson et al. | 428/198 |
| 4,215,692 | 8/1980 | Levesque | 162/92 |
| 4,306,929 | 12/1981 | Menikheim et al. | 156/290 |
| 4,329,763 | 5/1982 | Alexander et al. | 28/104 |
| 4,473,440 | 9/1984 | Ovans | 162/148 |
| 4,507,122 | 3/1985 | Levesque | 604/375 |
| 4,559,050 | 12/1985 | Iskra | 604/379 |
| 4,605,402 | 8/1986 | Iskra | 604/368 |
| 4,676,786 | 6/1987 | Nishino | 604/378 |
| 4,676,871 | 6/1987 | Cadieux et al. | 162/92 |
| 4,685,914 | 8/1987 | Holtman | 604/368 |
| 4,753,649 | 6/1988 | Pazdernik | 604/389 |
| 4,775,375 | 10/1988 | Aledo | 604/378 |
| 4,798,603 | 1/1989 | Meyer et al. | 604/378 |
| 4,992,324 | 2/1991 | Dubé | 428/226 |
| 5,124,195 | 6/1992 | Harpell et al. | 428/245 |
| 5,151,091 | 9/1992 | Glang et al. | 604/378 |
| 5,207,665 | 5/1993 | Davis et al. | 604/402 |

Primary Examiner—Randall L. Green
Assistant Examiner—P. Zuttarelli

[57] ABSTRACT

This invention relates to a novel absorbent structure and absorbent products containing this absorbent structure. More particularly, the absorbent structure of this invention is a flexible and retentive reservoir layer comprising a perf-embossed or tenderized peat board material.

8 Claims, 4 Drawing Sheets

UNITIZED SANITARY NAPKIN

This is a continuation of application Ser. No. 07/808,130, filed Dec. 13, 1991, now abandoned which is a continuation-in-part of Ser. No. 07/601,491 filed Oct. 22, 1990 now abandoned which is a continuation of Ser. No. 07/389,710 filed Aug. 4, 1989, now abandoned.

This application is related to commonly assigned, copending patent applications Ser. No. 242,271 (attorney Docket No. J&J 1238) entitled "Flexible Absorbent Board" and Ser. No. 242,274 (attorney Docket No. J&J 1267), entitled "Apparatus For Partially Slitting Absorbent Boards". This is a continuation-in-part of patent application Ser. No. 242,273, which is hereby incorporated by reference.

FIELD OF THE INVENTION

This invention relates to structures for absorbing body exudate. More particularly, the invention relates to absorbent structures which can be used in sanitary napkins, incontinence and wound dressing products and the like, which are unusually absorbent and retentive.

BACKGROUND OF THE INVENTION

Historically, women's sanitary protection products have been relatively unreliable in preventing staining of women's undergarments and outer garments during their menstrual periods. For example, large, bulky pads, which have high absorbency rates due to the use of hydrophilic materials such as wood pulp and rayon in their construction, nevertheless are often unable to capture or lock in retain absorbed menstrual fluid or dry out at the point of impact. They also tend to deform in use, leading to discomfort and the staining of undergarments and outer clothing. Even more recently developed, thinner pads, which contain polymer superabsorbent materials designed to aid in retaining fluids have high failure rates. Furthermore, both types of pads tend to buckle and deform in an undesirable manner under pressure such that they cannot maintain contact with the perineal area. This distortion can create canals or paths along which menstrual fluid can flow without being absorbed, thereby causing staining as the fluid is channelled away from the absorbent. Although multiple longitudinal channels may be desired, most prior art pads merely buckle to create a few large voids, which is undesirable.

When resilient material is added to pads in order to prevent deformation, the pads become uncomfortable and extremely expensive to make. Further, bulky pads are not significantly more failure-proof than thinner pads.

It is, therefore, an object of this invention to provide a sanitary protection product capable of effecting good gasketing and intimate contact with a woman's body during all phases or her activity while providing excellent absorbency and comfort due to the thinness of the product.

It is, therefore, an object of this invention to provide an absorbent structure capable of quickly absorbing and retaining large quantities of body fluid.

It is another object of that invention to provide a sanitary napkin capable of absorbing menstrual fluid quickly and efficiently and retaining that fluid in the absorbent structure of the napkin so as to limit failure.

Yet another object of this invention is to provide a sanitary napkin which is flexible and conformable, yet resistent to bunching and twisting.

Additional objects of this invention will became evident in the ensuing description.

SUMMARY OF THE INVENTION

The present invention features a unitized absorbent structure in which respective cover, transfer, and reservoir layers are selected for their capacity to receive, hold, disperse, and release fluids. Accordingly, with each such layer appropriately selected, there results a structure in which fluids are taken up at a rate which accomodates the exudate to which the structure is directed, and which permits the reservoir layer to receive, disperse, and retain the fluids on a relatively uniform basis throughout its width and length. Preferably, this is achieved in part through a positive density gradient (i.e., increasing density as a function of depth) from the cover sheet through a transfer layer and to and including the reservoir layer.

In preferred embodiments all three layers are unitized, but optionally for some applications, some shear may be permitted between select layers. In one embodiment of the present invention, respective discrete layers, each chosen for its density and its capacity to receive, disperse, and release fluids, are unitized by lamination one to the other. In an alternative embodiment, the layers are unitized by deposit in sequence, one on the other, in a continuous fiber deposition process, with transition areas thus being created between the layers. Irrespective of the degree or type of unitizing, the cover and transfer layers have respective successive increasing density, but both tend to avoid dispersion of fluid, instead tending to pass the fluid on to the level of next greater density. The reservoir layer, however, is selected for its capacity to disperse and to retain fluid, so that overall, the entire length and breadth of the reservoir will tend to be utilized, thereby to enhance overall efficiency of the structure.

An ancillary but highly desirable feature of such a structure is its flexibility, which in turn translates into a conformable product in which the fluid transfer properties are retained as the product deforms in use. Preferred embodiments employ dry flexibility on the same order as the undergarment itself or as pantyliners. On the other hand, as the product wets, the flexibility decreases somewhat in favor of increased resiliency.

Hence, products incorporating the principles of the present invention incorporate an absorbent structure which is not only extremely thin and flexible, but conformable and absorbent.

In the preferred embodiments, the cover and barrier layers extend beyond the edges of the fluid transfer layer and the reservoir layers and are sealed to each other around the periphery of the absorbent structure. Preferably, the cover and barrier layers are fused so as to create a fluid barrier seal around the periphery of the structure. This seal may be a thin line of fused area or a thicker line. If a thin line, the remainder of the peripheral area may be adhesively sealed.

This invention also relates to sanitary napkins which can be constructed using the absorbent structure of this invention. Preferably, a sanitary napkin of this invention is composed of an absorbent system and a liquid impermeable barrier layer. The absorbent system preferably includes a bulky, high-loft, low density cover containing hydrophilic fibers, a fluid transfer layer adjacent the cover and an absorbent reservoir layer adjacent the liquid transfer layer and the barrier layer. The absorbent system is laminated with all the layers bonded together such that they form a unitized structure.

In short, the absorbent structure of this invention is able to be useful in sanitary napkin products because it is attached to the wearer's undergarment under tension, which maintains its flatness against the undergarment. This maintains the surface constantly exposed and makes it coextensive with the undergarment, and therefore able to maintain coverage under dynamic stress situations.

The absorbent structure of this invention is also useful in infant and adult diapers, wound dressings and other products used to absorb body fluid. In the case of an incontinent device, at least one inter-layer interface may be unbonded to permit inter-layer shear.

DETAILED DESCRIPTION OF THE PREFERRED EMBODIMENTS

Figure 1:
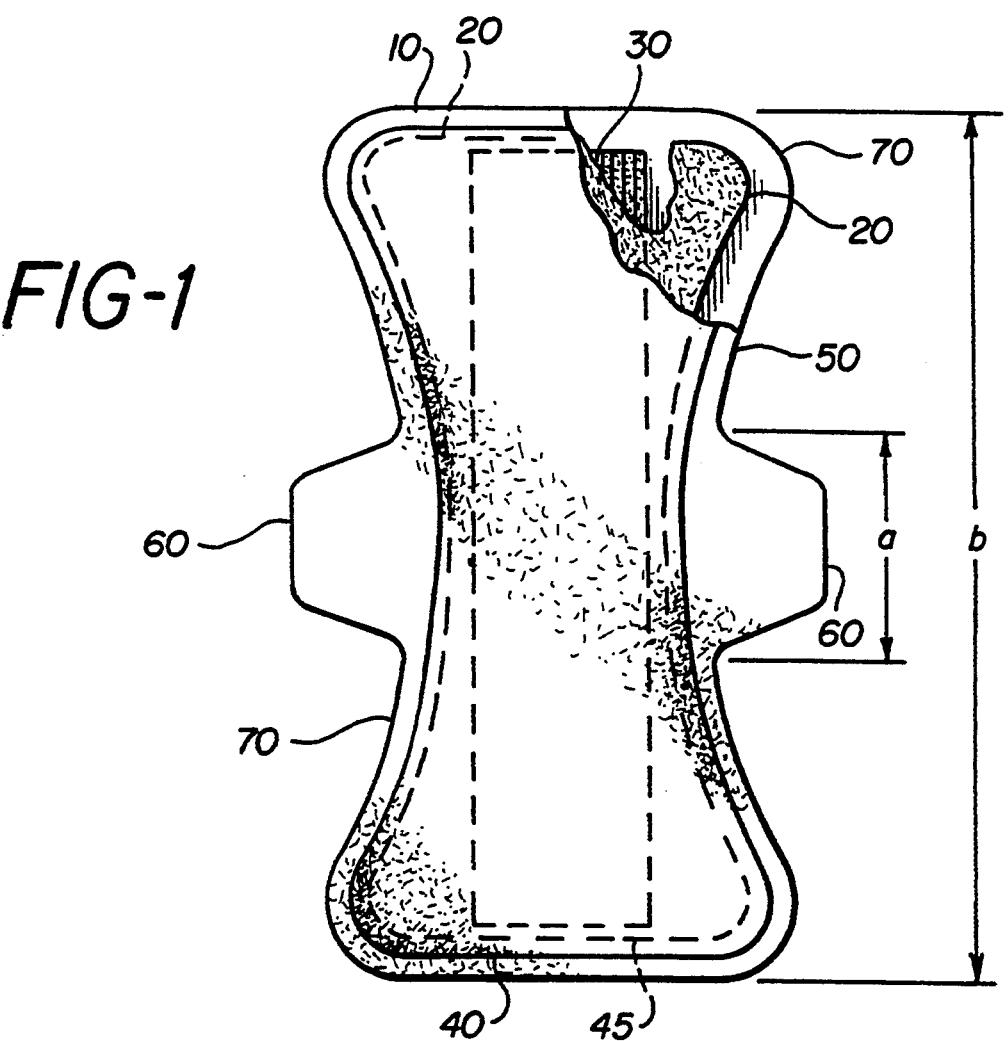
FIG. 1 is a plan view illustrating one embodiment of the sanitary napkin of this invention. A portion of FIG. 1 is broken away to illustrate the absorbent structure of the sanitary napkin.

Preferably, the absorbent structure of this invention has four elements: a cover layer, a fluid transfer layer, a reservoir layer and a barrier layer.

The absorbent structure of this invention has the ability to provide "dynamic coverage" of an undergarment. This means that the absorbent structure is large, and covers a large surface area, is extremely thin and yet very absorbent. Hence, in use, it acts essentially as a portion of the panty rather than as a discrete item. In addition, it provides protection no matter what activities the woman undertakes.

As defined herein, "substantial adherence" or "unitized" shall mean essentially integral contact, as by lamination or by continuous formation of respective layers through deposit of individual fibers. Also as used herein, the "capacity" of a given layer shall refer to its ability to accept fluid on one surface, to temporarily retain such fluid, and to release the same fluid to the next layer. Accordingly, "capacity" involves considerations both of physical retentiveness and time rate of change of fluid dispersion. In the following description, "capacity" is given dimension through physical as well as functional specifications (e.g., layer basis weight, fiber denier, pore size, thickness, density, permeability, wicking, holding capacity, etc.).

The cover layer is intended to substantially contact the body at the location at which fluid is being produced. In the case of a sanitary napkin, this would be the perineal area. The cover layer is preferably a relatively low density, bulky, high-loft nonwoven web material having a basis weight of between about 0.1 and 1.0 oz/yd$^2$. More preferably, the basis weight should be between about 0.25 and 0.75 oz/yd$^2$. Most preferably, it should be about 0.5 oz/yd$^2$. Fiber staple length is preferably between about 0.5 and 2 inches. More preferably, staple length should be between about 1.25 and 1.75 inches. Most preferably, it should be about 1.5 inches. However, so long as the cover retains the appropriate bulk and porosity, staple length is not critical. The fiber denier is preferably between about 1 and 3.5. More preferably, the denier is between about 2.5 and 3.25. Most preferably, it should be about 3. The cover layer may be composed of only one type of fiber, such as polyester, or it may be composed of bicomponent or conjugate fibers having a low melting point component and a high melting point component. The fibers may be selected from a variety of natural and synthetic materials such as nylon, polyester, rayon, (in combination with other fibers), cotton acrylic fiber and the like and combinations thereof.

Bicomponent fibers may be made up of a polyester core and a polyethylene sheath. The use of appropriate bicomponent materials results in a fusible nonwoven fabric. Examples of such fusible fabrics are described in U.S. Pat. No. 4,555,430, issued Nov. 26, 1985 to Mays. Using a fusible fabric increases the ease with which the cover layer may be bonded to the adjacent transfer layer and/or to the barrier layer.

The cover layer preferably has a relatively high degree of wettability, although the individual fibers comprising the cover may not be particularly hydrophyllic. The cover material should also contain a great number of relatively large pores. This is because the cover layer is intended to absorb body fluid rapidly and transport it away from the body and the point of deposition. Preferably, the fibers which make up the cover layer should not lose their physical properties when they are wetted, i.e. they should not collapse or lose their resiliency when subjected to water or body fluid. The cover may be treated to allow fluid to pass through it readily. The cover layer also functions to transfer the fluid quickly to the other layers of the absorbent structure. The cover should be able to transport fluid both vertically, to subjacent layers and horizontally, away from the point of deposition. Thus, the cover is preferably wettable, hydrophilic and porous. When composed of synthetic hydrophobic fibers such as polyester or bicomponent fibers, the cover may be treated with a surfactant to impart the desired degree of wettability.

Apertured polymer films having large pores may be used as cover materials, although they are not wettable. Because of their high porosity, such films accomplish the function of quickly transferring body fluid to the inner layers of the absorbent structure. Apertured coextruded films such as RETICULON ™ brand apertured film, for example, described in U.S. Pat. No. 4,690,679, are useful as cover layers in the absorbent structures of this invention. Another apertured film useful in the cover layer of the products of this invention is described in U.S. Pat. No. 4,342,314, issued Aug. 3, 1982 to Rodel et al.

An important aspect of the cover layer and the other layers of the absorbent structure of this invention is their pore size distribution. There should be many large pores in the cover layer, in order to ease the passage of fluid into the interior of the absorbent structure. Preferably, at least 15% of the pores should be greater than 300 μm in radius. More preferably, at least 30% of the pores should be greater than 300 μm in radius.

Another important attribute of the cover layer is water permeability. The cover layer should be highly fluid permeable, such that fluid passes through it quickly. Preferably, the cover layer has a water permeability of at least about 50 ft$^3$/ft$^2$/min. at a pressure differential of 0.17 psi. More preferably, the water permeability should be greater than about 60 t$^3$/ft$^2$/min. Most preferably, the water permeability should be greater than about 75 ft$^3$/ft$^2$/min.

Yet another important aspect of the cover layer is its ability to be wetted. In a basket wettability test of a hydrophilic cover, in which 5 grams (g) of material is placed in a basket in a reservoir and the time for the basket to sink is measured, the cover layer should be wettable enough such that it causes the basket to sink in less than 2 seconds. The Basket Sink Test is described in ASTM Standard publication and assigned ASTM No. D1117.

The cover may be embossed to the remainder of the absorbent structure in order to aid in promoting hydrophilicity by fusing the cover to the pulp of the next layer.

The cover layer, if it is composed of a fabric, should have a very low density, preferably less than about 0.10 g/cm$^3$, and more preferably, less than about 0.05 and even 0.02 g/cm$^3$ at 0.03 psi pressure differential. The cover layer should be the least dense of the layers which compose the absorbent structure of this invention. The other layers are progressively denser, thus establishing a density gradient, which functions to wick fluid away from the body. The cover layer may be relatively thick in comparison to conventional absorbent structure covers, but preferably should be less than about 0.10 to about 0.15 inch at 0.03 psi. More preferably, the cover should have a thickness of from about 0.01 to about 0.05 inch at 0.03 psi since a relatively thick cover contributes to the comfort of the absorbent structure when worn against the skin.

Adjacent to the cover layer on its inner side and bonded to the cover layer is the fluid transfer layer. The transfer layer provides a means of receiving body fluid from the cover layer and holding it until the highly-dense reservoir layer has an opportunity to absorb the fluid. The transfer layer is, preferably, more dense than and has a larger proportion of smaller pores than the cover layer. These attributes allow the transfer layer to contain body fluid and hold it away from the outer side of the cover layer, thereby preventing the fluid from rewetting the cover layer and its surface. However, the transfer layer is, preferably, not so dense as to prevent the passage of the fluid through the layer into the reservoir layer.

The transfer layer may be composed of fibrous materials, such as wood pulp, polyester, rayon, flexible foam (i.e. aminoether or low retention foam), or the like, or combinations thereof. For example, the transfer layer may be 100% pulp or contain pulp and rayon in a ratio of between about 97:3 and about 80:20. The transfer layer should have a relatively high degree of water permeability, have a pore size distribution which renders it capable of acting as a "holding tank" for the reservoir layer and it should retain its structural integrity in use, such that it is free of cracking, splitting or tearing and resists deformation when worn.

The transfer layer may also be composed of a blend of wood pulp with thermoplastic fibers for the purpose of stabilizing the layer and maintaining its structure integrity. For example, polyolefin fibers with the appropriate length and strength, such as low density polyethylene (such as PULPEX*, available from Hercules Corp.), or bicomponent fibers having polyethylene or polyester cores and a lower melting polyolefin sheath may be used, or polypropylene, polyvinylacetate, or other polyolefin fibers or themoplastic pulp equivalents and the like. Blending such fibers with wood pulp or the like adds stability and integrity to the transfer layer material. The ratio of thermoplastic fiber to pulp is preferably about 1:99 to about 50:50. More preferably, the ratio should be between about 3:97 and about 20:80. The fibers of the transfer layer may range in length from about 0.0117 in. for ground wood pulp to about 3 inches for the stabilizing thermoplastic fibers. Preferably, the fibers are between about 0.25 inches to about 1 inch in length if the nonwoven web of the transfer layer is intended to be stabilized by thermal bonding at the fibers' points of contact, although fiber length is not critical so long as the strength and integrety of the web is preserved.

Preferably, the basis weight of the web which comprises the transfer layer is from about 70 gm/m$^2$ to about 200 gm/m$^2$. More preferably, the basis weight of the transfer layer should be from about 3.00 oz/yd$^2$ to about 3.25 oz/yd$^2$. This basis weight is relatively higher than that of the cover layer.

The density of the transfer layer should also be higher than that of the cover layer. This increase in density aids in wicking the fluid away from the cover layer and retaining it in the transfer layer so as to prevent rewetting the surface of the cover layer. The cover layer is, therefore, drier and more comfortable against the skin than if it were subject to being rewetted by fluid. Preferably, the density should range from about 0.02 to about 0.10 g/cm$^3$ at 0.03 psi. More preferably, the density should be from about 0.04 g/cm$^3$ to about 0.08 g/cm$^3$. Most preferably, the density should range from about 0.06 g/cm$^3$ to about 0.08 g/cm$^3$.

The transfer layer should have a thickness of less than about 0.20 inches at 0.03 psi. More preferably, it should be between about 0.05 inches and 0.15 inches in thickness. Most preferably, it should be between about 0.06 and about 0.12 inches thick.

The water permeability of the transfer layer should be at least about 12 ft$^3$/ft$^2$/min. at 0.17 psi . This rate is relatively lower than that of the cover layer. Theoretically, the transfer layer should act as a "holding tank" for the body fluid as it flows through the cover layer and awaits discharge into the reservoir layer. The reservoir layer, while having a large fluid holding capacity, may be relatively slow in absorbing fluid, but holds it tenaciously. Thus, the transfer layer allows the reservoir layer to absorb fluid slowly while preventing the fluid from rewetting the cover layer. This aids in preventing failure of the absorbent structure. Bonded together, the cover and transfer layers should have a water permeability of at least about 10 ft$^3$/ft$^2$/min.

The transfer layer should be quite wettable, with a basket sink time of less than about 2 seconds. When constructed of stabilized wood pulp as hereinafter described, the typical pore size distribution of the transfer layer is such that about 10% of the pores are larger than 300 μm in radius and at least about 50% are smaller than 300 μm.

The transfer layer may be treated with surfactant on one or both sides in order to increase its wettability, although generally the transfer layer is relatively hydrophilic and may not require treatment. The transfer layer is preferably bonded on both sides to the adjacent layers, i.e. the cover layer and the reservoir layer.

The cover and transfer layer may also be made in a unitized manner by the use of varying density pulp fibers which may be laid, compressed and allowed to decompress. The heaviest density materials will remain on the bottom of the layer and the lower density materials will remain on the upper portion of the layer, thereby creating a low density cover segment and a higher density transfer segment.

Immediately adjacent to and bonded to the transfer layer is the fluid reservoir layer. The reservoir layer is preferably a highly dense absorbent layer having a fine porosity. It has a large fluid holding capacity and is extremely retentive. In essence, it acts as a capillary "pump" to absorb body fluid away from the transfer layer.

However, the reservoir layer need not be as rapidly wicking as the cover layer and the transfer layer. The basket sink time of the material of the reservoir layer may be as high as 5.0 seconds. Preferably, the reservoir layer is less than approximately 0.10 inch in thickness, and more preferably between about 0.045 and 0.070 inch at 0.03 psi. when constructed of compressed peat moss board as hereinafter described, the reservoir layer typically has a density of between about 0.20 g/cm$^3$ and 1.0 g/cm$^3$ at 0.03 psi. The average pore size of the dry compressed reservoir layer prior to wetting should be about 0.5 to 30 μm, preferably 0.5 to about 10 μm. In the wet state, the reservoir layer preferably has a pore size distribution such that less than about 10% of the pores are larger than 300 μm in radius and at least about 90% of the pores are smaller than 300 μm. If the reservoir layer is made of swellable, initially compressed material, the pore sizes change upon exposure to water, thus pore size distribution and/or porosity information is given in wet and dry states.

The reservoir layer should be capable of absorbing and retaining fluid without permitting it to elute through the layer, and so that the fluid does not flow back into the transfer and cover layers under normal use. It should also be extremely thin, but have a large capacity for holding fluids.

Most preferably, the reservoir layer is composed of compressed peat moss board. This board is made from sphagnum peat moss in accordance with processes delineated in U.S. Pat. No. 4,473,440 and patents referred to therein. The board may be formed by any of the methods set forth in U.S. Pat. No. 4,170,515 (issued to J-M LaLancette et al. on Oct. 9, 1979); U.S. Pat. No. 4,226,232 (issued to Y. Levesque on Oct. 7, 1980), U.S. Pat. No. 4,215,692 (issued to Y. Levesque on Aug. 5, 1980) and U.S. Pat. No. 4,507,122 (issued to Y. Levesque on May 26, 1985) and then subjected to the methods set forth in U.S. Pat. No. 4,473,440 (issued to K-J. Ovans on Sep. 25, 1984).

The peat moss board useful in the reservoir layer of the products of this invention may be made from a plurality of narrow, longitudinally extending strips disposed adjacent to one another and interconnected by an integral fibrous component extending between adjacent strips as described in copending patent application Ser. No. 242,271 filed Sep. 12, 1988 (attorney docket No. J&J 1238). The absorbent structure is preferably fabricated from a calendered peat moss board having a fibrous component admixed therewith, as set forth in U.S. Pat. No. 4,473,440. The fibrous component is suitably a natural or synthetic textile fiber such as rayon, polyester, nylon, acrylic or the like, having a length of from about 0.25 to 1.5 inches (preferably about 0.5 inches) and a denier of from about 1.0 to 5. The fibrous component may be present in an amount from about 2 to 20% by weight, most preferably from 4 to 8%. The absorbent board may also comprise other components such as wood pulp, synthetic wood pulp, thermomechanical pulp, mechanically ground pulp, polymers, surfactants, superabsorbents and the like.

The absorbent structure comprising of peat moss as the primary absorbent component is formed as a board by air or wet laying and calendering to obtain a relatively thin, i.e. from about 0.01 to 0.10 inch thick, relatively dense, i.e. from about 0.2 to 1.0 g/cm$^3$ sheet like structure. The structure may include a layer of Kraft tissue laminated on one or both surfaces of the peat moss layer. The absorbent board thus formed is a relatively thin structure similar to those described in the aforementioned U.S. patent references.

The absorbent peat moss board or other suitable compacted absorbent structure is processed to increase the flexibility thereof by partially severing the structure into a plurality of narrow strips which remain interconnected by an integral fibrous component of the structure. The board may be suitably severed by passing between a pair of rolls having a plurality of parallel spaced apart ridges or teeth extending circumferentially around the outer surface of the rolls. The two rolls are adjusted so that the opposing teeth are offset from each other without contact so that when the absorbent board is passed between the rolls, alternate strips of the friable board material are displaced relative to one another in the plane of the board. The displacement is sufficient to disrupt the friable absorbent material of the board such as the peat moss or wood pulp and delineate the individual strips without cutting or otherwise substantially disrupting the fibrous component of the board.

The partially severed product consists of a plurality of individual strips of the absorbent board having a width corresponding to the spacing of the teeth on the shearing rolls, and interconnected by the fibrous component extending between adjacent strips. The fibrous component provides a hinge-like action, and the resulting product has extreme transverse flexibility while maintaining transverse structural integrity. The partial shearing does not substantially affect flexibility in the longitudinal direction of the strips however, and if such flexibility is desired, the absorbent board may be embossed or micro corrugated in a generally transverse direction before or after the partial shearing operation.

In addition to increasing flexibility, the partial shearing of the absorbent board enhances the rate of liquid absorption by increasing the effective surface area of the board as a result of the edges of the slit material being available to the fluid. The partial shearing also imparts directional absorbent capacity to the absorbent boards since fluid wicks preferentially along the slits in the longitudinal direction of the material. By orienting the slit material in the longitudinal direction of a sanitary napkin or diaper, the incidence of edge failure in such products is consequently reduced.

The fibrous component extending between an interconnecting adjacent strips of absorbent material permits the absorbent element to be transported, rolled and handled during processing and assembly of absorbent products. The enhanced rate of fluid absorption and the directional absorption characteristics of the absorbent element permit it to be used directly as the primary absorbent in absorbent products with the resulting products being exceptionally thin, flexible and effective.

Another means of increasing flexibility of the peat moss board is to needle the peat moss board. This process also increases porosity and decreases the time for absorbing fluid. This needling process is described in British patent specification number 2,162,466.

Peat moss board has a large proportion of extremely tiny pores and capillaries which give it the ability to absorb an enormous capacity of fluid and retain it. The peat moss board swells as it absorbs fluid, however, this swelling does not cause it to lose its capacity for absorbing fluid. Rather, the swelling contributes to the ability of the reservoir layer to generally maintain the structural integrity of the absorbent structure in use. Peat moss board has the unique capability of "drying" adjacent materials by continuing to pull moisture away from them, over along time period such that little or no moisture remains in the adjacent materials. It can be made to be thin and flexible, if treated appropriately such as by partial slitting as described above, or by tenderizing in accordance with the process set forth in U.S. Pat. No. 4,605,402, without substantial loss of fluid holding capacity. The tenderizing process includes the steps of microcorrugating compressed board by passing the web through fluted intermeshing rolls and then perf embossing the board by using techniques such as those set forth in U.S. Pat. No. 3,837,827

Peat moss board prepared in accordance with the teachings of U.S. Pat. Nos. 4,473,440 and/or 4,507,122 are subjected to tenderizing treatment methods analogous to those described in U.S. Pat. No. 4,605,402 for highly compressed composite absorbent products which have superabsorbent materials dispersed therein. These manufacturing and tenderizing processes provide an absorbent flexible board structure comprising densified compressed peat moss board having a thickness of from about 0.01 to 0.10 inches and a density of from about 0.2 to 1.0 g/cm$^3$. In preferred embodiments the board comprises from about 2 to 20% by weight of the total weight of the board of a fibrous component selected from the group consisting of rayon, polyester, nylon or acrylic. In more preferred embodiments the fibrous component comprises fibers having a length of from about 0.25 to 0.75 inches and comprises from about 4 to 8% of the board by weight of the total weight of the board. In other preferred embodiments the board additionally comprises at least one kraft issue layer laminated to the board structure.

The above-described tenderizing process produces a board with increased flexibility and conformability as is demonstrated by the increased drapability of the tenderized board over similar non-tenderized peat moss board. This increased drapability provides an increased comfort factor for use of the tenderized absorbent board in sanitary napkins, adult incontinence briefs and diapers or in any other use where increased flexibility or drapability is advantageous.

Although peat moss board is the most preferred embodiment of the reservoir layer, there are many other highly absorbent and retentive material systems which can be used in the reservoir layer. For example, pulp-superabsorbent systems such as those described in U.S. Pat. No. 4,610,678 (Weisman, et al., Sep. 9, 1986) or U.S. Pat. No. 4,103,062 (Abetson et al., Jul. 25, 1978) may function as a reservoir layer of the product of this invention. Such absorbent structures contain a mixture of hydrophilic fibers such as wood pulp fluff and discrete particles of a water insoluble hydrogel such as silica gels or crosslinked polymers. Superabsorbent may be placed in certain areas of the reservoir layer where it may be needed more urgently than in others. For example, superabsorbent may be concentrated in the central portion or the end portions of the reservoir layer. The resulting absorbent structure may also be cut or tenderized to render it flexible and suitable for use in the products of this invention.

Melt blown fiber systems such as those described in U.S. Pat. No. 4,100,324 (Anderson et al., Jul. 11, 1978) may also be useful in making the reservoir layer of the absorbent structure of this invention. Another example of a densified layer which may be used as a reservoir layer in the absorbent structure of this invention is densified sugar cane pulp. In short, any highly-dense, highly-absorbent and highly-retentive absorbent material which can be made thin and flexible may function as material out of which acceptable reservoir layer may be made. The reservoir layer may be shaped three-dimensionally or two-dimensionally according to the desires of the manufacturer. Such absorbent structures may differ in density, pore size and other physical characteristics from the above-described peat moss board, while nevertheless possessing the liquid absorption and retention properties required for the reservoir layer.

The absorbent structures of this invention are necessarily bonded between all layers. Bonding not only preserves the physical integrity of the structure, it also improves the fluid transfer between layers. The absorbent structures of this invention may be laminated and/or embossed in order to improve the contact between layers.

However, a tissue layer may be placed between the reservoir and transfer layers. The tissue layer may act a carrier for the reservoir layer, in the case where portions of the reservoir layer may flake or separate from the remainder of the reservoir.

Figure 3:
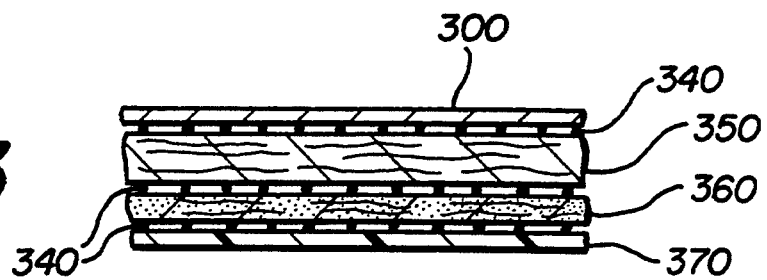
FIG. 3 is a cross-sectional view of one embodiment of the absorbent structure of this invention.

FIG. 3 illustrates one embodiment of the absorbent structure of this invention. Overlying the absorbent structure is the high-loft, high-bulk cover layer 300. Cover layer 300 is adhesively-bonded to transfer layer 350 with adhesive bonding 340, which has been randomly sprayed onto the inner surfaces of cover layer 300, transfer layer 350 and reservoir layer 360. Transfer layer 350 is, in turn, adhesively bonded to reservoir layer 360. Reservoir layer 360 is also bonded to impermeable barrier 370. Fluid enters the absorbent structure through highly porous cover layer 300. Cover layer 300 quickly transfers the fluid to transfer layer 350. Transfer layer 350 holds the fluid until reservoir layer 360 has an opportunity to absorb the fluid. The adhesive bonding 340 maintains intimate contact between the layers and enables them to effect a better transfer of fluid than if the layers were not bonded.

The absorbent structures of this invention are useful in sanitary napkin and other body fluid-absorbing products. The sanitary napkin products made in accordance with this invention are uniquely thin, flexible, absorbent and conformable yet resilient to stress exerted in the transverse, or x-direction when wet. Such sanitary napkins can be made to conform in shape to the crotch-portion of an undergarment. Preferably, they are hourglass-shaped and cover a large proportion of the undergarment's surface. However, they may be made in any configuration known to those skilled in the art.

Due to their flexibility, the sanitary napkins of this invention conform to the changes in the three-dimensional shape of undergarments as they are worn. In use, they form many fine longitudinal channels, or "fluting", which aid in fluid transport. Yet, the sanitary napkins of this invention are surprisingly resilient to stresses exerted in the transverse, or x-direction, when exposed to fluid. This provides a large surface area available for fluid uptake so as to substantially prevent failure.

In contrast, the sanitary napkins of the prior art tend to bunch or rope when worn, causing transverse creases and large longitudinal creases, causing large, undesirable voids in the absorbent sections. This decreases available surface area. This bunching is caused by the movement of the thighs, exerting forces across the x-direction of the absorbent. Bunching creates pockets or canals which divert fluid from the central absorbent system and from which fluid leaks from the pad onto the wearer's undergarment or body. The sanitary napkins of this invention, however, are resilient to bunching or roping despite their ability to conform to the movements of the undergarment.

Figure 2:
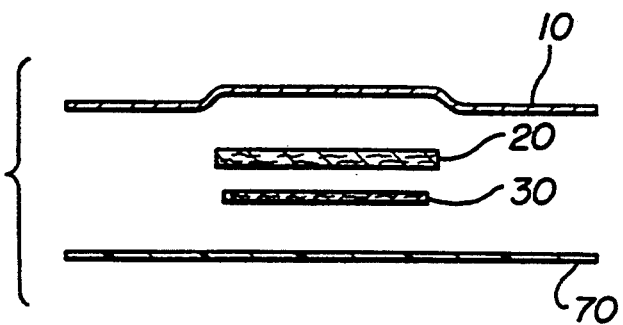
FIG. 2 is an exploded view of a cross-section of the sanitary napkin depicted in FIG. 1. It shows the absorbent structure without adhesive bonding between the layers.

A preferred embodiment of the sanitary napkin of this invention is depicted in FIGS. 1 and 2. The sanitary napkin of this invention contains a high-bulk, high-loft cover layer 10. Immediately adjacent and bonded to cover 10 is fluid transfer layer 20. Transfer layer 20 is composed of non-woven fabric of higher density than that of cover 10, as described above. Transfer layer 20 may be bonded to cover 10 with pressure-sensitive adhesive, thermosetting adhesive, hot melt adhesive or the like, which can be sprayed onto the surface of the layers or applied by printing. In the alternative, cover 10 and transfer layer 20 may contain thermoplastic fibers which can be exposed to heat and melted such that they form bonds between the layers.

Immediately adjacent to and bonded to transfer layer 20 is fluid reservoir layer 30. Reservoir layer 30 is preferably shaped rectangularly and extends substantially along the longitudinal axis of the napkin. However, reservoir layer 30 preferably does not abut the longitudinal end 40 of cover 10 nor does it abut the longitudinal ends 45 of transfer layer 20. This construction is intended to substantially prevent end failure by obviating contact between the fluid-containing portion of the napkin and the end of the napkin, thus allowing fluid to flow to and remain in the reservoir layer, although this aspect is not critical. This construction is also preferred at the lateral sides 50 of the napkin. Optionally, reservoir layer 30 is adhesively bonded to impermeable barrier layer 70. Barrier layer 70 is bonded to cover layer 10 around the periphery of the napkin. Preferably, a thin peripheral seal is created between the edge of transfer layers 20 and the extreme periphery of the barrier and cover layers to provide a fluid barrier. The area outside the peripheral seal, which may be made by heat, ultrasonic or mechanical means, may be adhered using pressure sensitive adhesive or the like.

Optionally, the sanitary napkins of this invention have relatively small tabs 60 extending from their longitudinal sides. Such tabs 60 should extend no more than about one-third the length of the lateral side 50 of the napkin, i.e. length a—a should be less than one-third of length b—b. These tabs should not have absorbent material from the reservoir or transfer layers extending across their surface, although the cover may optionally be coextensive with tabs 60. The function of the tabs is merely to secure the napkin to the undergarment at its lateral sides 50. Tabs 60 also aid in maintaining the napkin's structural integrity in the x-direction when subjected to stress from thigh motion and fluid absorption. If cover material is coextensive with the tabs in order, it may assist in wicking fluid away from the side area and afford ease in processing.

The sanitary napkins of this invention may be attached to the crotch portion of the undergarment with adhesives, such as hot-melt adhesives and the like. These adhesives may be applied to the bottom of the barrier portion of the absorbent structure in various patterns, including complete adhesive coverage, parallel longitudinal lanes, several parallel horizontal lines, a line of adhesive following the perimeter of the structure, as a "cross", or the like. Velcro attachments may be employed at the longitudinal ends of the napkin to attach it to the undergarment, or adhesive tabs may be placed at the sides and/or at the four corners of the structure. Alternatively, the sanitary napkin of this invention may be attached to a belt which encircles the waist of the wearer.

Figure 4:
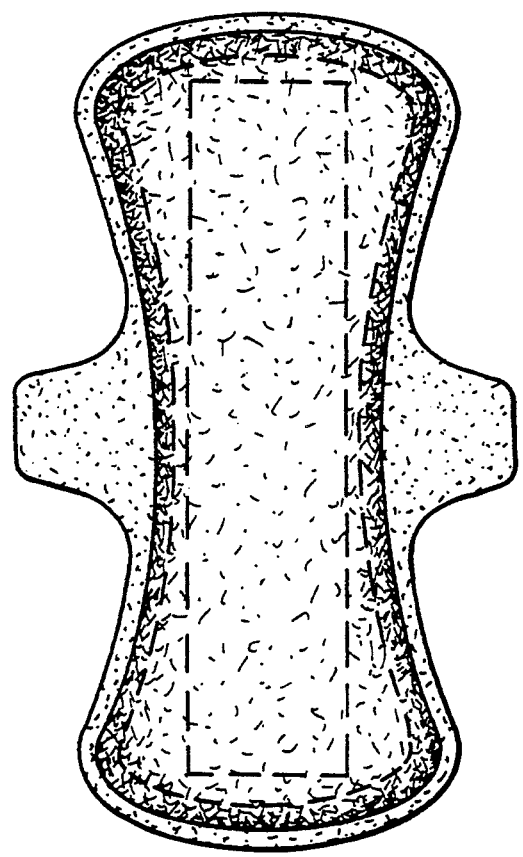
FIG. 4 is a plan view of one embodiment of the sanitary napkin of this invention.
Figure 5:
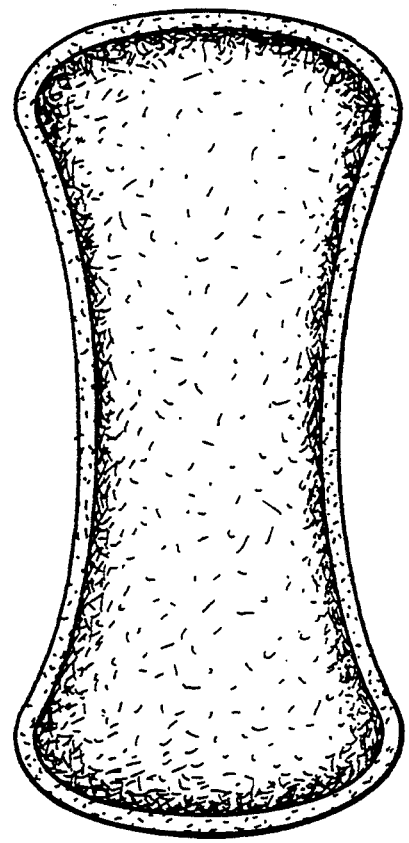
FIG. 5 is a plan view of another embodiment of this invention.

FIGS. 4 and 5 illustrate additional embodiments of the sanitary napkins of this invention. FIG. 4 illustrates a napkin having slightly rounded lateral ends. FIG. 5 illustrates a napkin which does not have tabs at its longitudinal sides.

The sanitary napkins made in accordance with this invention should have little or no fluid strikeback, i.e. menstrual fluid, once absorbed, should not reappear on the surface of the napkin.

The thickness of the sanitary napkins of this invention measured in the z-direction should be no greater than about 0.250 inch when dry at 0.03 psi. Preferably, it should be less than 0.200 inch thick. When peat moss board is used as a reservoir layer, the thickness should be no greater than about 0.400 inch when wet, as peat moss board expands upon wetting. If another type of reservoir layer is used the thickness should also be no greater than about 0.400 inch when wet.

After the sanitary napkin of this invention is constructed and bonded together, the entire pad (or, optionally but less preferably, only the cover) may be embossed using a pattern which extends along the longitudinal axis of the napkin. Of course, the embossing pattern can be of any shape or conformation, such as straight lines, wavy lines or a design, so long as it is oriented along the longitudinal direction. This embossing pattern promotes the distribution of fluid not only in the z-direction, but in the longitudinal direction.

The theoretical water holding capacity (as measured by a Gravimetric Absorbency Testing System as set forth in U.S. Pat. No. 4,357,827) of the sanitary napkins of this inventions should be at least about 65 cc and, preferably, at least about 75 cc of 1% saline solution. The amount of force required to create the initial lateral deformation of a napkin of this invention should be no more than about 200 g when the napkin is dry and no more than about 250 g when the napkin is wet, although the force can exceed 400 g when dry if the reservoir layer has not been treated to render it more flexible.

Reservoir layers can be made much more flexible when treated.

The degree of force needed to bend the napkin of this invention a distance of 1.5 cm in the z-direction should be no more than about 50 g when dry and no more than about 55 g when wet. Preferably, the force should be no more than about 35 g when dry and less than about 30 g when wet.

The degree of torque needed to bend the sanitary napkin of this invention 90° around its longitudinal, or y-axis should be no greater than about 200 g-cm when dry and no more than about 315 g-cm when wet, although it may be greater if the reservoir layer is not treated to render it more flexible. Preferably, if is less than about 120 g-cm when dry and less than about 200 g-cm when wet.

The following examples are illustrative of certain preferred embodiments of this invention. However, in no way do these examples serve to limit this invention.

EXAMPLE 1

A sanitary napkin in accordance with this invention was made by bonding together the following elements: (1) 100% Enka brand polyester fibrous nonwoven carded web the fibers having a denier of 3, a staple length of 1.5 inches; the nonwoven web having a basis weight of 0.5 oz/yd$^2$, made by through-air bonding with no restraint; (2) a fluid transfer layer made of aerobonded stabilized pulp [10% bicomponent Enka®, 60% rayon, 80% pulp, 4% Nacan anionic vinyl acrylic copolymer binder]; (3) a creped, partially slit peat moss board reservoir layer and (4) an impermeable barrier made of polyethylene. The layers were bonded using fine lines of hot melt, pressure sensitive adhesive, which was printed onto the layers. This adhesive may be sprayed, so long as the adhesive lines are fine enough not to interfere with permeability. The cover and the polyethylene barrier were bonded around the periphery of the napkin using the adhesive and exposure to heat and pressure. The entire structure was laminated and embossed at a temperature of about 220° F. and a pressure of about 100 psi. The structure was then embossed along the longitudinal axis using a pattern of multiple sinusoidal lines.

The pore size distribution of each layer was measured by desorption on a porous plate. Pore size distribution is determined by measuring the amount of fluid desorbed at a particular hydrostatic pressure. This can be done using the apparatus described in U.S. Pat. No. 4,357,827. The amount of fluid desorbed at various pressures can be correlated to the pore size in accordance with the Laplace equation, $p = 2\gamma \cos\theta / R_c$ where p is capillary pressure, $\gamma$ is the surface tension of the liquid, $\theta$ is the contact angle at the liquid-solid-air interface and $R_c$ is the capillary radious. The height of the capillary rise can be obtained by dividing the pressure, p, by the density of the fluid and g, gravitational force. This process is explained in more detail in Chatterjee, *Absorbency*, Elsevier Science Publishers, B. V., 1985, pp. 36-40. The resulting distribution is set forth in Table IA.

The components of the napkins of this Example were measured for wickability by placing them in a position 90° relative to the horizontal plane with their ends submerged in water. The perpendicular distance along which the water was absorbed was measured after 5 minutes, 30 minutes, 1 hour and 2 hours. The results are set forth in Table IB. Table IB demonstrates that the cover layer is not very wickable, the transfer layer is somewhat wickable, while the reservoir layer is extremely wickable.

EXAMPLE 2

The components of the napkin of Example 1 were measured in the z-direction and their densities calculated under four levels of pressure, 0.03 psi, 0.10 psi, 0.20 psi and 0.50 psi. The thicknesses and densities of each layer are set forth in Table II. The total thickness of the sanitary napkin product of Example 1 at 0.03 psi is about 0.158 inches.

EXAMPLE 3

The thickness of a sanitary napkin made in accordance with Example 1 was measured when dry under four pressures, 0.03 psi, 0.10 psi, 0.20 psi and 0.50 psi. Three other sanitary protection products were also measured at each of these pressures, as follows: STAYFREE* brand Maxipads available from Personal Products Co., ALWAYS* brand Maxipads available from The Procter & Gamble Co., and STAYFREE* brand Minipads available from Personal Products Co. These pads were then totally saturated with water, and their thicknesses again measured at various pressures. The dry and wet thicknesses measured are set forth in Table III. This test measured dry z-direction deformability and wet collapse due to pressure. Full-period protection pads are considerably thicker than those of Example 1, both when wet and dry. The STAYFREE* brand Minipads, Maxipads and ALWAYS brand Maxipads tend to collapse when wet, as can be seen from Table III. However, the pads of Example 1 swell and retain their structure when wet.

EXAMPLE 4

A Gravimetric Absorbency Test was performed on various sanitary protection products in order to indicate the theoretical water holding capacity of the products. The test procedure is outlined in *Absorbency* (P. K. Chatterjee, Elsevier Science Publishers, B. V., 1985, p. 67), and in U.S. Pat. No. 4,357,827. The results of this test are set forth in Table IV. A product made in accordance with Example 1 had a theoretical water holding capacity of about 83 cc, or about 10 times its weight in water, on or about the same order of magnitude as a STAYFREE* brand Maxipad and an ALWAYS* brand Maxipad, which had a capacity of about 12 times their respective weights. Yet, the product of Example 1 is considerably thinner than the commercially available maxipads. The theoretical water holding capacity of other sanitary protection products, including LIGHT DAYS* brand panty liner, commercially available from Kimberly-Clark Co., a CAREFREE* brand panty shield, commercially available from Personal Products Co. and a SURE & NATURAL* brand Maxishield, commercially available from Personal Products Co. was also tested.

EXAMPLE 5

Figure 6:
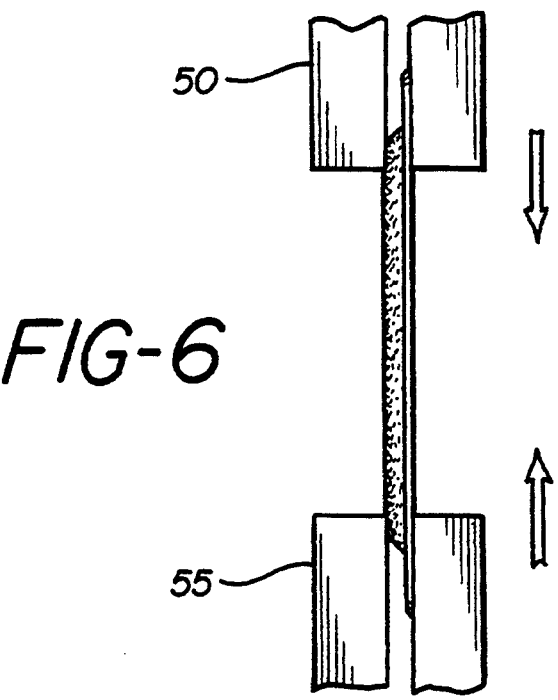
FIG. 6 is a perspective view of an illustration of side compression test equipment.

A side compression initial deformation test, which measures the amount of force needed in the x-direction to begin to deform a pad, was performed in order to determine the x-direction resistance to deformation of various sanitary protection products. In this test, the sanitary napkin was held in a vise-like structure as illustrated in FIG. 6. The vise-jaws 50, 55 were then brought toward one another at the rate of 50 mm/min.

and the force required to first produce a bend in the sanitary napkin was measured using an Instron tester(-Tensile and Compression Tester). The measurements were first made using various dry sanitary protection products. Fifteen cc of ersatz menstrual fluid was then deposited in the center of the napkins and they were tested again. The results of this test are set forth in Table V. Table V shows that, in dry side compression tests, the sanitary napkin of Example 1 is relatively easy to deform initially and would tend, therefore, to be conformable to the wearer's motion and undergarments. However, when wet, the force required to create an initial deformation increases, thus indicating that the product of Example 1 tends to resist collapse when wet, thus preserving its resiliency and structural integrity.

EXAMPLE 6

Figure 8:
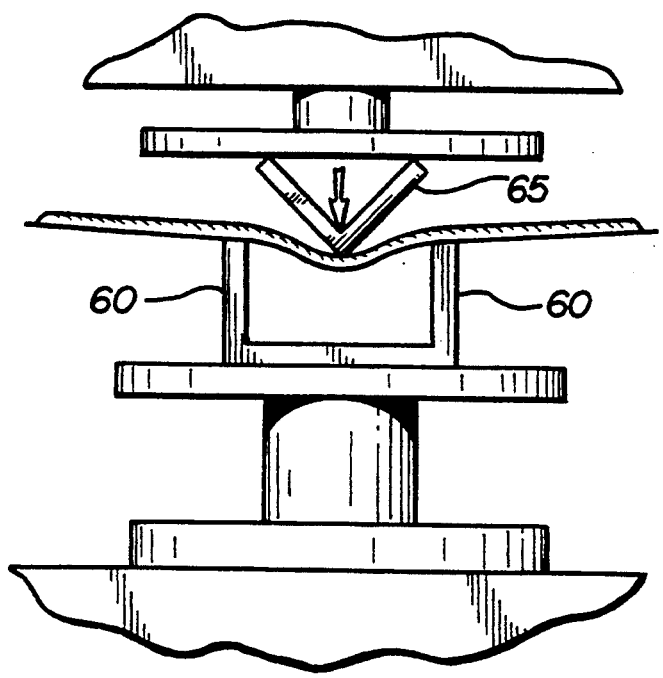
FIG. 8 is a perspective view of deformation bonding testing equipment.

A dry bending test, in which the degree of force needed for certain degrees of z-direction deformation, was performed to determine the degree of flexibility of the products of Example 1 compared to other full-menstrual period protection products. The apparatus used to perform this test is depicted in FIG. 8. A sanitary protection product rests on arms 60 which are 6.4 cm apart. Each arm is 0.6 cm thick. Head 65 is brought downward against the napkin to deform it at a rate of 50 mm/min. Various napkins were tested both in a wet and a dry state. The deformation distance is measured as well as the load required to achieve that degree of deformation. The load required was measured using an Instron Tester. The results of this Example are set forth in Tables VIA and VIB. In fact, the flexibility is on the order of magnitude of that of small, thin pantyliner-type products. This z-direction flexibility is retained when wet.

EXAMPLE 7

Figure 9:
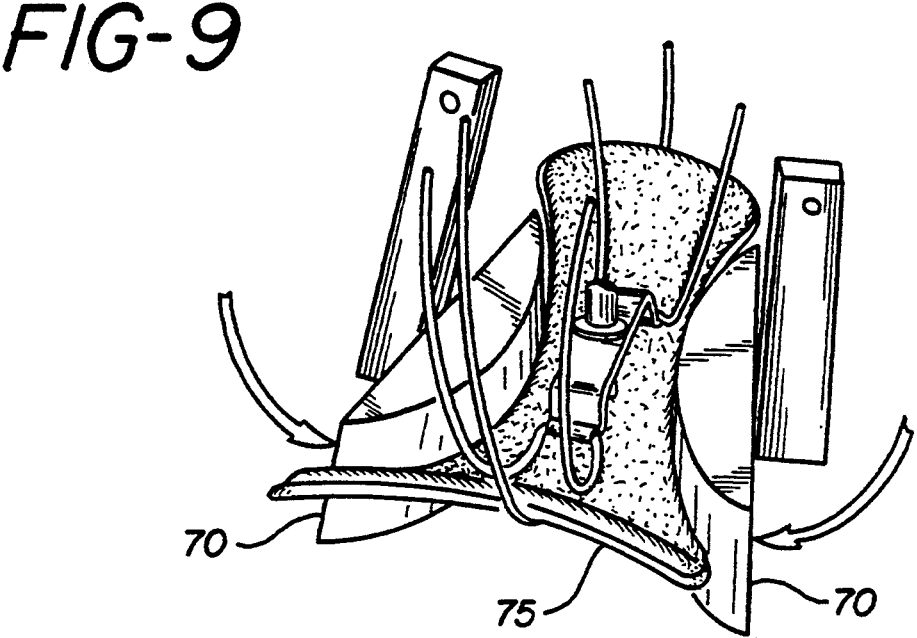
FIG. 9 is a perspective view of resilience-compression testing equipment.

A resilience-compression test was performed in order to determine the conformability of the napkins of Example 1. Results of this test indicate that the products of this invention are considerably more conformable and flexible both wet and dry than any other commercial pad tested. Convex, thigh-shaped forms 70 were positioned at the longitudinal sides of each napkin 75 without exerting force on the napkin as depicted in FIG. 9. The initial force needed to compress the dry napkin at a head speed of 14 cycles/min. from 2.5" to a 1" gap was measured using an Instron Tester. Then, 15 cc of ersatz menstrual fluid was deposited on the middle of the pad and the compression motion continued. The results of this test are set forth in Table VII. In all pads except those made in accordance with Example 1, there was a drop in the amount of force required to compress the napkin without crushing it. In the case of the pads of Example 1, the product exhibits an increase in compressive resistance when wet. All other products exhibit a decrease in compressive resistance. Thus, the napkin of this invention is flexible, yet remains resilient when wet.

EXAMPLE 8

Figure 7:
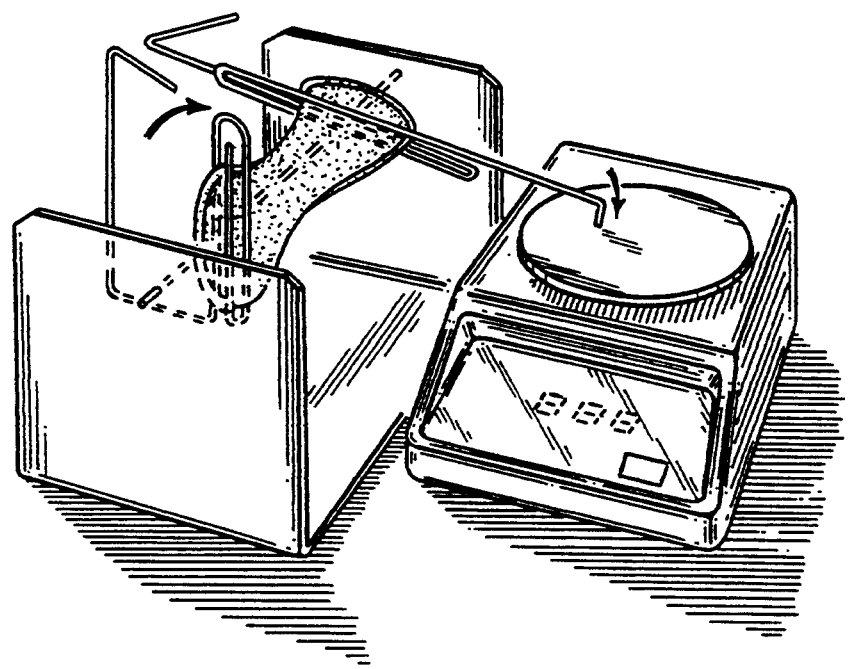
FIG. 7 is a perspective view of torsion testing equipment.

A torsion test was performed to determine the torque required to twist a napkin around its longitudinal axis 90° both in a wet and a dry state. The napkin of Example 1 demonstrated the ability of retaining its resiliency and, in fact, increasing it, when wet. The napkins were clasped into a wire vise at each longitudinal end as depicted in FIG. 7. Each vise had an extension, one of which rested upon a scale. The other extension could be used to twist the napkin in a clockwise direction 90° around its longitudinal axis. The scale indicates the force required to twist the napkin. As shown in Table VIII, the napkin of Example 1 required considerably more force to twist it when wet than when dry. This indicates that the napkin actually becomes considerably more resilient when wet and will tend to resist bunching and roping in use.

EXAMPLE 9

In order to determine the wetback properties of various sanitary protection products, a wetback test was performed. Fifteen cc of ersatz menstrual fluid was deposited on a napkin in its center. After 15 minutes, a circular piece of NU-GAUZE* nonwoven rayon fabric commercially available from Johnson & Johnson Ltd. 4.5 cm in diameter was placed over the location at which the fluid was deposited. A plastic sheet was placed over the napkin and a 500 g weight also 4.5 cm in diameter was placed over the gauze for 5 minutes. After 5 minutes, the weight, plastic and gauze was removed, the gauze weighed and the volume of fluid absorbed by the gauze determined. The napkin made in accordance with Example 1 allowed the least amount of fluid to rewet the gauze. The results of this test are set forth in Table IX.

EXAMPLE 10

An impact capacity test was performed on several sanitary napkins; including a napkin made in accordance with Example 1. The napkins were held in a 45 degree angle to the horizontal plane. Twenty-five cc of ersatz menstrual fluid was deposited onto the angled napkins. The napkins were each weighed to determine the amount of fluid retained. A STAYFREE TM brand regular maxipad having a modified entangled fiber polyester cover retained 4 cc; a STAYFREE TM brand regular maxipad having an apertured fibrous cover (165 apertures per square inch) retained 13 cc; a napkin made according to Example 1 retained 22 cc; an ALWAYS TM brand maxipad retained 25 cc; and a SURE & NATURAL TM brand Maxishield retained 17 cc.

EXAMPLE 11

A sanitary napkin was prepared in accordance with Example 1, except that the reservoir layer was a four (4)-gram tenderized peat moss board insert rather than a partially slit, creped board. Upon testing for absorbent-related properties, the sanitary napkin of this example exhibited only trace amounts of wetback after wetting with 15 ml of ersatz menstrual fluid. The 45° impact capacity was 22 cc. The therotetical water holding capacity for an 8.00 g. sample was 81 cc. The dry sample was 0.124 in. thick and, when wet, 0.307 in. thick. Testing for physical properties revealed that the dry sample was 0.124" thick at 0.03 psi, 0.114" at 0.10 psi, 0.104" at 0.20 psi and 0.091" at 0.50 psi. The initial deformation peak upon side compression was 194 g. dry and 207 g. wet. The dry bending test showed that the load required to deform the pad 0.5 cm was 15 g; to deform the pad 1.0 cm was 24 g; and to deform the pad 1.5 cm was 26 g. When wet, the load required to deform the pad 0.5 cm was 37 g; to deform the pad 1.0 cm was 47 g; and to deform the pad 1.5 cm was 51 g. The resilience-compression test indicated that 0.59 kg of force was required to compress the dry pad and 0.55 g. of force was required to compress the wet pad. 282 g. cm of torque were required to twist the pad 90° when wetted.

EXAMPLE 12

A sanitary napkin was prepared in accordance with Example 1, except that the reservoir layer was a pair of compressed pulp board inserts from SURE & NATURAL TM Maxishields containing superabsorbent instead of a creped, partially-slit board. Upon testing for absorbent-related properties, the sanitary napkin of this example exhibited 0.06 g. of wetback fluid after wetting with 15 ml of ersatz menstrual fluid. The 45° impact capacity was 20 cc. The theoretical water holding capacity for an 9.21 g. sample was 81 cc. The dry sample was 0.138 in. thick and, when wet, 0.313 in. thick. Testing for physical properties revealed that the dry sample was 0.138" thick at 0.03 psi, 0.124" at 0.10 psi, 0.113" at 0.20 psi and 0.100" at 0.50 psi . The initial deformation peak upon side compression was 429 g. dry and 165 g. wet. The dry bending test showed that the load required to deform the pad 0.5 cm was 33 g; to deform the pad 1.0 cm was 57 g; and to deform the pad 1.5 cm was 68 g. When wet, the load required to deform the pad 0.5 cm was 23 g; to deform the pad 1.0 cm was 28 g; and to deform the pad 1.5 cm was 30 g. The resilience compression test indicated that 2.86 kg of force was required to compress the dry pad and 0.94 g of force was required to compress the wet pad. 164 g. cm of torque were required to twist the dry pad 90°. 316 g. cm of torque were required to twist the pad 90° when wetted. If this board were tenderized or partially slit or otherwise treated for flexibility, it would exhibit more flexibility.

EXAMPLE 13

Various cover materials which may be useful in the products of this invention were tested for water permeability by constructing a "plug" made of the cover material. The plug was applied and subjected to a pressure difference of about 0.17 psi in order to induce a steady flow through the plate and plug. The water permeability was then calculated using Darcy's Law, on: $q = -K \, \Delta P/L_o$, where q is the volume flex in the flow direction, $\Delta P$ is the net pressure head that causes the flow and $L_o$ is the length of the sample in the direction of flow. K is a proportionality constant representing the flow conductivity of the porous medium with respect to the fluid.

An Enka ® polyester fiber cover having a basis weight of about 0.6 oz/yd$^2$, a density of 0.035 g/cc and a thickness of 0.25" was Sample 1. A bicomponent fiber Enka ® cover having a basis weight of about 0.63 oz/yd$^2$ was tested as Sample 2. A 100% thermally bonded polypropylene fiber cover having a basis weight of about 0.53 oz/yd$^2$, a density of about 0.191 g/cc and a thickness of about 0.009" was Sample 3. Sample 4 was an apertured fibrous cover having 165 apertures per square inch. Sample 5 was the cover of a CAREFREE* brand panty shield; Sample 6 was a fibrous polyethylene cover of a STAYFREE* brand maxipad; and Sample 7 was the cover an ALWAYS* brand maxipad; Sample 8 was the cover of LIGHTDAYS* brand panty liner; Sample 9 was the cover of a STAYFREE* brand minipad; and Sample 10 was the cover of a SURE & NATURAL* brand maxishield. An increasing number of plies was measured to determine multiple-ply permeability. The results of this test are set forth in Table X. Table X demonstrates that Samples 1–3, the covers of this invention, have extremely high fluid permeability, i.e. 60 ft$^3$/ft$^2$/min.

Pore size determinations were made using Samples 1 and 3. The results of these determinations are set forth in Table XA.

EXAMPLE 14

Various fibrous webs suitable for use as transfer layers in the absorbent structure of this invention were tested for water permeability as in Example 14. A 94% stabilized pulp, 6% rayon web having a basis weight of about 3.3 oz/yd$^2$, (or 110 g/m$^2$) a density of 0.035 g/cc and a thickness of 0.12" was tested as Sample X. The water permeability of Sample X was 34.0 ft$^3$/ft$^2$/min.

Sample Y was 100% Kraft ground pulp web having a bsis weight of about 3.3 oz/yd$^2$, (or 110 g/m$^2$) a density of about 0.035 g/cc and a thickness of about 0.124". Sample Y had a water permeability of about 25.4 ft$^3$/ft$^2$/min.

Sample Z was a stabilized pulp web containing 80% pulp and 20% Pulpex* (thermally bonding fibers avaiabe commercially from Hercules Corp. Sample Z had a basis weight of about 3.3 oz/yd$^2$ (or 110 g), a density of 0.092 g/cc and a thickness of 0.119". Sample Z had a water permeability of about 17.7 ft$^3$/ft$^2$/min.

Samples X, Y and Z were also tested for wettability using a sink basket. Sample X had a basket sink time of 1.5 sec. Sample Y had a basket sink time of 1.2 sec. Sample Z had a basket sink time of 2.0 sec.

The 90° wicking test was also conducted on Samples X, Y and Z. Sample X wicked 4.5 cm. along its length; Sample Y, 5.5 cm; and Sample Z, 3.5 cm.

Pore size determinations using the porous plate method were performed upon Samples X, Y and Z, as well. The results of this test are set forth in Table XI.

Of course, the absorbent- system of this invention may be useful in many absorbent products known to those of skill in the art. For example, the absorbent system of this invention may be used in infant and adult diapers, adult incontinence devices, wound dressings and the like.

TABLE IA

| | PORE SIZE DETERMINATION | | | |
|---|---|---|---|---|
| Height (cm) | Pore Radius (microns) | Cover | Transfer | Reservoir |
| −1 | <1470 | 26.6% | 5% | 1.5% |
| −5 | 1470–295 | 55.3% | 17.8% | 6.2% |
| −10 | 295–147 | 18.1% | 37.6% | 11.7% |
| −20 | 147–74 | | 27.8% | 29.3% |
| −25 | 74–59 | | 3.0% | 5.2% |
| −40 | 59–37 | | 5.0% | 9.2% |
| <−40 | <37 | | 3.8% | 36.9% |

TABLE IB

| | 90° WICKING TEST | | |
|---|---|---|---|
| Rise vs. Time (cm) | Cover Layer (cm) | Transfer Layer (cm) | Reservoir Layer (cm) |
| 5 Min. | <0.5 | 3 (pulp) 5 (rayon) | 9.0 |
| 30 Min | <0.5 | 3 (pulp) 5 (rayon) | 15.5 |
| 1 Hour | <0.5 | 3 (pulp) 5 (rayon) | 20.0 |
| 2 Hours | <0.5 | 3 (pulp) 5 (rayon) | 23.5 |

TABLE II

THICKNESS AND DENSITY OF PRODUCT COMPONENTS AT VARYING PRESSURES

| (Basis Wt) PRESSURE | COVER LAYER (20 g/sq m) | | TRANSFER LAYER (105 g/sq m) | | RESERVOIR LAYER (400 g/sq m) | |
|---|---|---|---|---|---|---|
| | THICKNESS | (DENSITY g/cc) | THICKNESS | (DENSITY g/cc) | THICKNESS | (DENSITY g/cc) |
| 0.03 psi | 0.025" | (0.035) | 0.067" | (0.068) | 0.066" | (0.240) |
| 0.10 psi | 0.021" | (0.041) | 0.058" | (0.079) | 0.061" | (0.260) |
| 0.20 psi | 0.018" | (0.048) | 0.054" | (0.085) | 0.058" | (0.280) |
| 0.50 psi | 0.013" | (0.067) | 0.045" | (0.102) | 0.051" | (0.310) |

TABLE III

DRY AND WET THICKNESS (INCHES) OF SANITARY PROTECTION PRODUCTS

| Pressure (psi) | Example 1 Dry | Example 1 Wet | STAYFREE* Maxipad Dry | STAYFREE* Maxipad Wet | ALWAYS* Maxipad Dry | ALWAYS* Maxipad Wet | STAYFREE* Minipad Dry | STAYFREE* Minipad Wet |
|---|---|---|---|---|---|---|---|---|
| 0.03 | 0.139 | 0.308 | 0.763 | 0.636 | 0.701 | 0.709 | 0.321 | 0.274 |
| 0.10 | 0.128 | 0.277 | 0.691 | 0.611 | 0.633 | 0.652 | 0.280 | 0.227 |
| 0.20 | 0.118 | 0.252 | 0.638 | 0.550 | 0.587 | 0.590 | 0.253 | 0.192 |
| 0.50 | 0.105 | 0.206 | 0.538 | 0.430 | 0.518 | 0.468 | 0.196 | 0.145 |

TABLE IV

THEORETICAL WATER HOLDING CAPACITY

| | Total Wt. (g) | Thickness (0.03 psi) (Dry/Wet) | Capacity (cc) | % Collapse |
|---|---|---|---|---|
| STAYFREE* Maxipad | 11.0 | 0.723/0.479 | 133 | 33.7% |
| ALWAYS* Maxipad | 10.0 | 0.760/0.590 | 123 | 22.4% |
| STAYFREE* Minipad | 3.85 | 0.342/0.218 | 16 | 36.4% |
| LIGHT DAYS* Pantyliner | 2.03 | 0.100/0.095 | 13 | 5% |
| CAREFREE* Panty Shield | 1.92 | 0.178/0.282 | 16 | −58.4% |
| Example 1 | 8.60 | 0.143/0.309 | 83 | −116% |
| SURE & NATURAL* Maxishield | 7.93 | 0.281/0.362 | 142 | −28.8% |

TABLE V

INITIAL DEFORMATION PEAK (SIDE COMPRESSION)

| | DRY COMPRESSION (g) | WET COMPRESSION (15 cc) (g) |
|---|---|---|
| ALWAYS* Maxipad | 709 | 603 |
| STAYFREE* Maxipad | 565 | 426 |
| Example 1 | 152 | 200 |
| STAYFREE* Minipad | 113 | 88 |
| LIGHTDAYS* Pantyliner | 88 | 148 |
| CAREFREE* Panty Shield | 54 | 65 |
| SURE & NATURAL* Maxishield | 290 | 224 |

TABLE VI

DRY BENDING TEST (Deformation vs. Load)

| Deformation (cm) | 0 | 0.5 | 1.0 | 1.5 |
|---|---|---|---|---|
| CAREFREE* Panty Shield | 0 | 9 | 14 | 16 |
| LIGHTDAYS* Panty Liner | 0 | 14 | 22 | 23 |
| Example 1 | 0 | 21 | 30 | 31 |
| STAYFREE* Minipad | 0 | 21 | 29 | 34 |
| STAYFREE* Maxipad | 0 | 55 | 90 | 150 |
| ALWAYS* Maxipad | 0 | 64 | 114 | 187 |
| SURE & NATURAL* Maxishield | 0 | 24 | 55 | 70 |

TABLE VIB

WET BENDING TEST (Deformation vs. Load)

| Deformation (cm) | 0 | 0.5 | 1.0 | 1.5 |
|---|---|---|---|---|
| CAREFREE* Panty Shields | 0 | 9 | 12 | 13 |
| LIGHTDAYS* Pantyliner | 0 | 53 | 64 | 71 |
| Example 1 | 0 | 16 | 20 | 21 |
| STAYFREE* Minipad | 0 | 23 | 29 | 34 |
| STAYFREE* Maxipad | 0 | 58 | 89 | 135 |
| ALWAYS* Maxipad | 0 | 91 | 142 | 214 |
| SURE & NATURAL* Maxishield | 0 | 36 | 51 | 61 |

TABLE VII

RESILIENCE - COMPRESSION TEST

| | DRY (kg) | WET (kg) |
|---|---|---|
| ALWAYS* Maxipad | 4.00 | 1.98 |
| STAYFREE* Maxipad | 2.91 | 1.54 |
| STAYFREE* Minipad | 2.09 | 1.41 |
| LIGHTDAYS* Pantyliner | 1.99 | 1.80 |
| CAREFREE* Panty Shield | 1.50 | 1.09 |
| Example 1 | 0.50 | 0.53 |
| SURE & NATURAL* Maxishield | 1.83 | 0.89 |

TABLE VIII

TORSION TEST (90° Twist)

| Torque (g cm) | DRY | WET |
|---|---|---|
| STAYFREE* Maxipad | 479 | 508 |
| ALWAYS* Maxipad | 338 | 367 |
| STAYFREE* Minipad | 110 | 125 |
| Example 1 | 112 | 190 |
| LIGHTDAYS* Pantyliner | 54 | 51 |
| CAREFREE* Panty Shield | 42 | 37 |
| SURE & NATURAL* Maxishield | 282 | 205 |

TABLE IX

WET BAG TEST

| Product | Volume Picked up By Fabric (cc) |
|---|---|
| STAYFREE* Maxipad (Polyester Cover) | 0.38 |
| STAYFREE* Maxipad (Apertured Fibrous Cover) | 0.40 |
| ALWAYS* Maxipad | 0.01 |
| Example 1 | Trace |
| LIGHTDAYS PANTYLINER (3 cc Deposit) | 0.20 |
| NEW FREEDOM* Thin Pad | 0.16 |
| SURE & NATURAL* Maxishield | Trace |

TABLE X

COVER PERMEABILITY (ft³/ft²/min. under 0.17 psi)

| Sample # | No. of plies: | | | | |
|---|---|---|---|---|---|
| | 1 | 2 | 3 | 4 | 5 |
| 1 | 83.6 | 74.2 | 62.9 | 54.9 | — |

TABLE X-continued

| | COVER PERMEABILITY ($ft^3/ft^2$/min. under 0.17 psi) | | | | |
|---|---|---|---|---|---|
| | No. of plies: | | | | |
| Sample # | 1 | 2 | 3 | 4 | 5 |
| 2 | 66.8 | 56.1 | 45.5 | 40.9 | 34.3 |
| 3 | 60.2 | 46.6 | 34.6 | 28.3 | 22.8 |
| 4 | 54.0 | 30.1 | 15.6 | 12.3 | — |
| 5 | 51.5 | 44.7 | 37.0 | 34.8 | 24.2 |
| 6 | 49.7 | 37.6 | 27.2 | 20.2 | 15.7 |
| 7 | 49.7 | 26.1 | 19.5 | 10.7 | 9.35 |
| 8 | 49.4 | 32.6 | 25.6 | 18.7 | 13.4 |
| 9 | 44.6 | 27.6 | 20.2 | 14.0 | 10.2 |
| 10 | 41.7 | 24.0 | 13.6 | 8.46 | 6.75 |

TABLE XA

| PORE SIZE DETERMINATION OF COVER (WET STATE) | | |
|---|---|---|
| PORE RADIUS (mm) | SAMPLE 1 | SAMPLE 3 |
| >1470 | 26.6% | 0.0% |
| 1470 to 735 | 15.5% | 0.0% |
| 735 to 490 | 15.5% | 3.0% |
| 490 to 368 | 17.7% | 4.0% |
| 368 to 294 | 6.6% | 8.0% |
| 294 to 245 | 6.6% | 3.0% |
| 245 to 210 | 4.4% | 13.0% |
| 210 to 184 | 2.2% | 16.0% |
| <184 | 4.9% | 47.0% |

TABLE XI

| PORE SIZE DETERMINATION OF TRANSFER LAYER (WET STATE) | | | |
|---|---|---|---|
| PORE RADIUS (mm) | SAMPLE X | SAMPLE Y | SAMPLE Z |
| >1470 | 15.5% | 9.2% | 13.4% |
| 1470 to 295 | 17.0% | 15.3% | 19.5% |
| 295 to 147 | 12.5% | 13.3% | 12.1% |
| 147 to 98 | 10.0% | 14.8% | 12.1% |
| 98 to 74 | 10.0% | 14.3% | 20.3% |
| 74 to 59 | 10.9% | 8.1% | 10.2% |
| 59 to 37 | 16.2% | 16.0% | 7.4% |
| <37 | 7.9% | 9.0% | 4.5% |

EXAMPLES 15-20

Drapability Testing of Absorbent Peat Moss Board

Peat moss boards (reservoir layers) having the following characteristics were prepared in accordance with the teachings of U.S. Pat. Nos. 4,473,440 and 4,507,122:

In accordance with the patented methods a calendared peat board web is subjected to perf-embossing. The perf-embossing step provides first perforating the densified calendared web, then sequentially embossing the resulting material in both the machine direction and perpendicular to the machine direction.

Perf-embossing or "PERF", is performed by passing the web between a pair of rolls provided with intermeshing and non-contacting teeth perforating the web by shearing action mainly to open the structure of the cellulosic material to reduce its stiffness, while densifying other regions of the web. The overlap between the teeth of the perforating rolls is set at approximately 35 thousandths of an inch (mils). This setting may vary according to the web thickness, humidity and other factors.

The second step of the perf-embossing operation consists of embossing the perforated web in the machine direction and perpendicular to the machine direction (i.e. cross-direction) by passing the web between a pair of rolls with intermeshing longitudinally extending flutes. The flutes imprint lines on each surface of the web by locally compacting the fibrous material under the effect of mechanical compression.

It will be appreciated that the perpendicular or cross-direction embossing rolls alter the structure of the web in two significant aspects. Miniature hinges extending transversely to the pulp fluff web provide an increase in the web's flexibility in the longitudinal direction along the imprint lines and the fiber density in the vicinity of the lines is increased by virtue of the mechanical compaction necessary to form the impressions. As a result, a distinct fiber density profile is imparted to the pulp fluff web, consisting of high and low fiber density zones alternating in the machine direction. A desirable consequence of the achieved variable fiber density is a selective alteration of the fluid absorption characteristics of the web, creating spaced apart high density, relatively less-absorbent areas, providing a fluid wicking action in a transverse direction to the web.

Embossing the web in the machine direction is accomplished by passing the web between parallel rolls having circumferentially extending and intermeshing flutes. This embossing operation, creates longitudinal lines to impart a fiber density profile of alternating high and low fiber density areas in a transverse direction of the web as well as providing longitudinal hinge lines.

Examples 15-17 are peat boards having the following characteristics:

| | Ex. 15 | Ex. 16 | Ex. 17 |
|---|---|---|---|
| Basis weight $gm/m^2$ | 230 | 355 | 405 |
| Thickness | 0.023" | 0.034" | 0.028" |
| Bulk density | 0.40 g/cc | 0.41 g/cc | 0.57 g/cc |

Additionally, Examples 18-20 are peat boards having basis weights Of 200 $gm/m^2$ (Ex. 18): 325 $gm/m^2$ (Ex. 19); and 405 $gm/m^2$ (Ex. 20) and are prepared and subjected to identical levels (0-3) of tenderizing as indicated above for example 15-17.

Each board was perf-embossed according to three levels of performing (PF) and embossing in the machine direction (MD) and perpendicular to the machine direction (PMD) of $^1$(0.015"PF, 0.025"MD and 0.020"PMD); $^2$(0.050"PF, 0.035"MD, and 0.030"PMD); and $^3$(0.095"PF, 0.035"MD and 0.035"PMD). The corresponding "Drape Value" of the boards was measured against non-perf-embossed boards.

Drape Value is measured by subjecting an 8 inch diameter disk of materials to a 360° deformation by forcing a ring having an internal diameter of 7.25" past the 8 inch diameter material supported between two disks of 7.00" and 6.85" diameter respectively. As a consequence, only the outer rim of the material is subjected to 360° deformation (i.e. a fringe which is 0.575" wide. Drape is defined as the force in grams needed to deform the sheet at peak value.

The average drape values (amount of weight in grams to deform the sheet at peak value for examples 18-20 are provided below for levels 0-3 of perf-embossing.

| | Ex. 18 | Ex. 19 | Ex. 20 |
|---|---|---|---|
| Level 0 | 1938 gm | 3483 gm | 7617 gm |
| Level 1 | 448 gm | 466 gm | 1037 gm |
| Level 2 | 147 gm | 232 gm | 637 gm |

-continued

|         | Ex. 18 | Ex. 19 | Ex. 20 |
|---------|--------|--------|--------|
| Level 3 | 100 gm | 135 gm | 374 gm |

In hygienic products where drape and flexibility corresponds with acceptable comfort levels for the wearer it is preferred to provide an absorbent product with a drape value in the range of 200 to 800 gms, whereby less than 200 gms would be a limp product having poor tensile strength and greater than 800 gms levels of perf-embossing would be Level 1 for Ex. 18; Levels 1 and 2 for Ex. 19 and Levels 2 and 3 for Ex. 20.

One can see that the degree of drape modification obtained by perf-embossing is quite appreciable from the untreated board to each of the three levels of perf-embossing.

The percentage of residual force from the original (non-tenderized) board (100%) as compared to the same boards subjected to three levels of perf-embossing or tenderizing is indicated below:

|                      | Residual Force Differentiation |        |        |
|----------------------|--------|--------|--------|
| Level of Perf-Emboss | Ex. 15 | Ex. 16 | Ex. 17 |
| Level 0 (no treatment) | 100%  | 100%   | 100%   |
| Level 1              | 23%    | 13.3%  | 13.6%  |
| Level 2              | 7.6%   | 6.6%   | 8.2%   |
| Level 3              | 5.2%   | 3.9%   | 4.9%   |

An assessment of the flexibility of the material is made with a cantilever device wherein a strip of material is depressed by slipping it over an edge; the length of overhang is measured when the tip of the specimen causes a 41.5° with the horizontal. A short overhang relates to a flexible and highly drapable material.

In addition to drapability, the levels of tenderizing or perf-embossing impact on the tensile strength of the board and its wicking properties. While a board subjected to high levels of perf-embossing (e.g. Level 3) is the most flexible drapable and conformable (hence more comfortable to a wearer of the absorbent product) it is also weaker in terms of tensile strength and will not wick as well as less tenderized boards (e.g. Levels 1 and 2). The relative tensile strengths and wicking ability (as indicated by percent of fluid pick-up at a portion of the board and its pick up upon rewetting) is indicated below:

|                      | Board Tensile Strength* |        |        |
|----------------------|--------|--------|--------|
| Level of Perf-Emboss | Ex. 16 | Ex. 17 | Ex. 18 |
| Level 0 (no treatment) | 3.92 | 5.73   | 13.40  |
| Level 1              | 1.60   | 0.52   | 3.90   |
| Level 2              | 0.41   | 0.28   | 1.87   |
| Level 3              | 0.12   | 0.17   | 0.75   |

*Pounds per inch of board per ply at a crosshead speed of 10.5 inch/minute.

|                      | Board Rewetting* |        |        |
|----------------------|--------|--------|--------|
| Level of Perf-Emboss | Ex. 18 | Ex. 19 | Ex. 20 |
| Level 0              | 67/50/52 | 50/53/40 | 35/40/35 |
| Level 1              | 106/75/68 | 103/72/53 | 58/62/42 |
| Level 2              | 125/70/57 | 106/76/53 | 94/50/43 |
| Level 3              | 144/108/91 | 131/84/73 | 96/63/52 |

*Percentage pick-up of saline solution of a viscose nonwoven sponge placed at a point of liquid impact on the board whereby five times the weight of the board in liquid is applied to the board. The amount of liquid as a function of weight of the sponge which is then absorbed by the sponge is measured at time intervals of wetting and rewetting of 5 min/15 min/30 min.

As can be seen the higher the level of perf-embossing or tenderizing the higher the wet back value (the 5 minute value offering the largest span in wet back when compared to its control). The untenderized controls have practically the same wet back at the three time intervals whereby it becomes efficacious in a short time.

What is claimed is:

1. A unitized absorbent structure having respective cover, transfer, and reservoir layers, characterized in that:
    a) at least two of said respective layers are in physical contact with one another such that fluid transfer is promoted therebetween;
    b) said respective layers have a predetermined increasing density gradient from the cover layer to the reservoir layer;
    c) each of said layers has preselected fluid retention and transfer capacity;
    d) said cover and transfer layers tend to promote transfer to the next subsequent layer in preference to dispersion of fluid over their length and breadth, while said reservoir layer tends to promote dispersion and retention of fluid throughout its length and breadth, and
    e) said fluid reservoir layer comprising densified compressed peat moss board and an integral fibrous component whereby the board has a thickness of from about 0.01 to 0.10 inches and a density of from about 0.2 to 1.0 g/cm$^3$ and the board has been rendered more flexible by partially severing the structure into a plurality of narrow strips which remain interconnected by the integral fibrous component and wherein the fluid reservoir layer has a pore size distribution in the wet state such that between about 90% and 100% of the pores are less than 300 μm in radius and about between 0% and 10% of the pores are greater than 300 μm in radius.

2. The unitized absorbent structure of claim 1 additionally comprising at least one kraft tissue layer laminated to the fluid reservoir layer.

3. The unitized absorbent structure of claim 1 wherein the fluid reservoir layer has a drape value in the range of from 200 to 800 grams.

4. The unitized absorbent structure of claim 1 wherein the fluid reservoir layer has a total weight and the integral fibrous component is selected from the group consisting of rayon, polyester, nylon, and acrylic and is from about 2 to 20% by weight of the total weight.

5. The unitized absorbent structure of claim 4 wherein the fluid reservoir layer has a drape value in the range of from 200 to 800 grams.

6. The unitized absorbent structure of claim 4 wherein the integral fibrous component comprises fibers having a length of from about 0.25 to 0.75 inches and a denier of from about 1.0 to 5.

7. The unitized absorbent structure of claim 6 wherein the fluid reservoir layer has a drape value in the range of from 200 to 800 grams.

8. The unitized absorbent structure of claim 6 whereby the fluid reservoir layer has a total weight and the integral fibrous component is from 4 to 8% by weight of the total weight.

* * * * *